(12) United States Patent
Dong et al.

(10) Patent No.: US 6,406,881 B2
(45) Date of Patent: Jun. 18, 2002

(54) DOSING AND DEVELOPMENT OF ANTIMICROBIAL AND ANTIVIRAL DRUGS DETERMINED BY RESTRICTION OF RESISTANT MUTANT SELECTION

(75) Inventors: Yuzhi Dong, Bayside; Karl Drlica, New York; Xilin Zhao, Mt. Vernon, all of NY (US)

(73) Assignee: The Public Health Research Institute of the City of New York, Newark, NJ (US)

( * ) Notice: Subject to any disclaimer, the term of this patent is extended or adjusted under 35 U.S.C. 154(b) by 0 days.

(21) Appl. No.: 09/901,296

(22) Filed: Jul. 9, 2001

Related U.S. Application Data (62) Division of application No. 09/405,683, filed on Sep. 24, 1999, now Pat. No. 6,265,181.

(51) Int. Cl.[7] .............................. C12Q 1/18; C12Q 1/02; C12Q 1/04; C12Q 1/00

(52) U.S. Cl. ............................... 435/32; 435/29; 435/34; 435/4

(58) Field of Search ......................... 504/161; 514/663, 514/712, 372; 435/4, 29, 34, 5, 32

(56) References Cited

U.S. PATENT DOCUMENTS 5,322,834 A * 6/1994 Hsu ........................... 504/156

OTHER PUBLICATIONS

Fred C. Tenover et al., "The Epidemiology of Bacterial Resistance to Antimicrobial Agents," Evans AS and PS Brachman, Eds., Plenum Medical Book Co.: NY, Chapter 3, pp. 83–93, 1998.
Stuart B. Levy, "Multidrug Resistance—A Sign of the Times," N. Eng. J. Med. 338:1376–1378, 1998.
D. Milatovic et al., "Development of Resistance during Antibiotic Therapy," Eur. J. Clin. Microbiol., 6(3):234–244, 1987.
Gordon L. Archer, "*Staphylococcus aureus*: A Well–Armed Pathogen," Clin Infec. Dis. 26:1179–1181, 1998.
Thomas R. Frieden et al., "The Emergence of Drug–Resistant tuberculosis in New York City," N. Engl. J. Med. 328(8):521–526, 1993.
Kent A. Sepkowitz et al., "Trends in the Susceptibility of Tuberculosis in New York City, 1987–1991," Clin. Infec. Dis. 18:755–759, 1994.
Pablo J. Bifani et al., "Origin and Interstate Sread of a New York City Multidrug–Resiistant *Mycobacterium tuberculosis* Clone Family," J. Am. Med. Assoc. 275(6):452–457, 1996.
Chen Xu et al., "Fluoroquinolone Resistance Associated with Specific Gyrase Mutations in Clinical Isolates of Multidrug–Resistant *Mycobacterium tuberculosis*," J. Infect. Dis. 174:1127–1130, 1996.

R. Coninx et al., "First–line tuberculosis therapy and drug–resistant *Mycobacterium tuberculosis* in prisons," The Lancet 353:969–973, 1999.
P.N. Gaunt et al., "Ciprofloxacin resistant Campylobacter spp. in humans: an epidemiological and laboratory study," J. Antimicrob. Chemother 37:747–757, 1996.
Kirk E. Smith et al., "Quinolone–Resistant *Campylobacter Jejuni* Infections in Minnesota, 1992–1998," N. Engl. J. Med. 340(20):1525–1532, 1999.
Hubert Ph. Endtz et al., "Quinolone resistance in campylobacter isolated from man and poultry following the introduction of fluroquinolones in veterinary medicine," J. Antimicrob. Chemother. 27:199–208, 1991.
Ian Phillips, "Bacterial mutagenicity and the 4–quinolones," J. Antimicrob. Chemother. 20:771–773, 1987.
Alan B. Bloch et al., "Nationwide Survey of Drug–Resistant Tuberculosis in the United States," JAMA 271(9):665–671, 1994.
Marisa Moore et al., "Trends in Drug–Resistant Tuberculosis in the United States, 1993–1996," JAMA 278(10):833–837, 1997.
Yuzhi Dong et al., "Fluoroquinolone Action against Mycobacteria: Effects of C–8 Substitutents on Growth, Survival, and Resistance," Antimicrob. Agents Chemother. 42(11):2978–2984, 1998.
Xilin Zhao et al., "DNA topoisomerase targets of the fluoroquinolones: A strategy for avoiding bacterial resistance," Proc. Natl. Acad. Sci. U.S.A. 94:13991–13996, 1997.
F. Baquero et al., "Strategies to Minimize the Development of Antibiotic Resistance," J. Chemother. 9:Suppl. n. 3:29–37, 1997.
Yuzhi Dong et al., "Effect of Fluoroquinolone Concentration on Selection of Resistant Mutants of *Mycobacterium bovis* BCG and *Staphylococcus aureus*," Antimicrob. Agents Chemother. 43(7):1756–1758, 1999.

(List continued on next page.)

*Primary Examiner*—Christopher R. Tate
*Assistant Examiner*—Patricia A Patten
(74) *Attorney, Agent, or Firm*—Fish & Richardson P.C.

(57) ABSTRACT

The invention is based on the discovery that, for many drugs (e.g., antiviral or antimicrobial drugs such as antifungal or antibacterial drugs, including bacteriocidal or bacteriostatic drugs) and many pathogen strains (e.g., viral, fungal, or bacterial pathogens), a concentration of drug can be identified at which drug-resistant mutant pathogen strains are not selected. This concentration is herein referred to as the "mutant prevention concentration" (MPC). Maintaining serum concentrations of the drug above the MPC throughout a course of treatment should severely restrict selection of drug-resistant mutants. Additionally, it is discovered that drug-resistant mutant pathogens are selected exclusively within a drug concentration window, termed the "mutant selection window" (MSW). A quantitative expression of this window, which we call the "window index" (WI), is defined as the ratio of the MPC to the MIC. The window index is characteristic of a given drug and a given pathogen.

19 Claims, 9 Drawing Sheets

OTHER PUBLICATIONS

H. Stass et al., "Pharmacokinetics, Safety, and Tolerability of Ascending Single Doses of Moxifloxacin, a New 8–Methoxy Quinolone, Administered to Healthy Subjects," Antimicrob. Agents Chemother. 42(8):2060–2065, 1998.

Thomas Moulding et al., "Fixed–Dose Combinations of Antituberculosis Medications to Prevent Drug Resistance," Ann. Intern. Med. 122:951–954, 1995.

East African Hospital and British Medical Research Council, "Comparative Trial of Isoniazid Alone in Low and High Dosage and Isoniazid Plus Pas in the Treatment of Acute Pulmonary Tuberculosis in East Africans," Tubercle 40:83–102, 1960.

Marc Lipsitch et al., "The Population Dynamics of Antimicrobial Chemotherapy," Antimicrob. Agents Chemother. 41(2):363–373, 1997.

Second East African/British Medical Research Council Study, "Controlled Clinical Trial of Four Short–Course (6–Month) Regimens of Chemotherapy for Treatment of Pulmonary Tuberculosis," Lancet 2:1100–1106, 1974.

G.R. Mason et al., "Emergence of MDR TB During Standard Therapy in AIDS," Am. J. Respir. Crit. Care Med. 1997; 155:A221.

Andrew Vernon et al., "Acquired rifamycin monoresistance in patients with HIV–related tuberculosis treated with once–weekly rifapentine and isoniazid," Lancet 353:1843–1847, 1999.

Manju Mahajan et al., "Initial and acquired drug resistance of *Mycobacterium tuberculosis* in East Delhi," J. Commun Dis. 28(1):15–19, 1996.

Gianni Acocella et al., "Comparative Bioavailability of Isoniazid, Rifampin, and Pyrazinamide Administered in Free Combination and in a Fixed Triple Formulation Designed for Daily Use in Antituberculosis Chemotherapy," Am. Rev. Respir. Dis. 138:886–890, 1988.

Nalin Rastogi et al., "In Vitro Activities of Fourteen Antimicrobial Agents Against Drug Susceptible and Resistant Clinical Isolates of *Mycobacterium tuberculosis* and Comparative Intracellular Activities Against the Virulent H37Rv Strain in Human Macrophages," Curr. Microbiol. 33:167–175, 1996.

K.D. Stottmeier et al., "Determination of Drug Susceptibility of Mycobacteria to Pyrazinamide in 7H10 Agar," Am. Rev. Respir. Dis. 96:1072–1075, 1967.

Conrado P. Aranda, "Pyrazinamide," Tuberculosis, Rom WN and SM Garay, Eds., Little Brown, and Co.: Boston. p. 799–802, 1996.

Baquero, "Resistance to Quinolones in Gram–Negative Microorganisms: Mechanisms and Prevention," Eur Urol. 1990; 17(suppl. 1):3–12.

Ben Yang Zhao et al., "Fluoroquinolone Action Against Clinical Isolates of *Mycobacterium tuberculosis*: Effects of a C–8 Methoxyl Group on Survival in Liquid Media and in Human Macrophages," Antimicrobial Agents and Chemotherapy, 43(3):661–666, 1999.

* cited by examiner

| Compound | C8 | X | Y | Z |
|---|---|---|---|---|
| Ciprofloxacin | H | H | H | H |
| HM1 | H | CH3 | H | H |
| HM2 | H | CH3 | H | CH3 |
| HE1 | H | C2H5 | H | H |
| HNE | H | H | C2H5 | H |
| HNIP | H | H | C3H7 | H |
| OH | O-CH3 | H | H | H |
| OM1 | O-CH3 | CH3 | H | H |
| OM2 | O-CH3 | CH3 | H | CH3 |
| OE1 | O-CH3 | C2H5 | H | H |
| ONE | O-CH3 | H | C2H5 | H |
| ONIP | O-CH3 | H | C3H7 | H |
| FH | F | H | H | H |
| FM1 | F | CH3 | H | H |
| FM2 | F | CH3 | H | CH3 |
| FE1 | F | C2H5 | H | H |
| FNE | F | H | C2H5 | H |
| FNIP | F | H | C3H7 | H |
| ClM1 | Cl | CH3 | H | H |
| ClM2 | Cl | CH3 | H | CH3 |
| BrM1 | Br | CH3 | H | H |
| BrM2 | Br | CH3 | H | CH3 |

DOSING AND DEVELOPMENT OF ANTIMICROBIAL AND ANTIVIRAL DRUGS DETERMINED BY RESTRICTION OF RESISTANT MUTANT SELECTION

CROSS REFERENCE TO RELATED APPLICATION

This application is a division of U.S. Ser. No. 09/405,683, filed Sep. 24, 1999 is now U.S. Pat. No. 6,265,181.

STATEMENT AS TO FEDERALLY SPONSORED RESEARCH

This invention was made with Government support under Grant No. AI35257 awarded by the National Institutes of Health. The Government may have certain rights in the invention.

FIELD OF THE INVENTION

The invention relates generally to methods for determining activity and suitable dosage levels for antimicrobial and/or antiviral drugs to restrict selection of resistant mutants.

BACKGROUND OF THE INVENTION

For any given microbial or viral pathogen (e.g., bacterial, fungal, or viral pathogen), there typically exists a characteristic concentration of a specified antimicrobial or antiviral drug (hereafter "drug"), or combination of drugs, at which recovery of microbial colonies or viral plaques from drug-containing cultures sharply decreases. This concentration is referred to as the "minimum inhibitory concentration" (MIC), and is conventionally defined with reference to a specific percent inhibition of pathogen growth. Thus, for example, the concentration of drug at which 99% of pathogen growth is inhibited is labelled $MIC_{99}$. In spite of the sharp decrease in pathogen growth at the MIC, a small but finite fraction are often able to grow in the presence of the drug. These pathogens are termed "drug-resistant." Drug resistant mutants arise spontaneously within pathogen populations. When a pathogen population is treated with a drug for an extended period of time (e.g., one or more days), resistant mutants proliferate while drug-sensitive, wild-type cells do not. Eventually, the pathogen population becomes dominated by the resistant mutants. This process, which is called "selection", can occur both in vitro and in vivo. The selection process is responsible for the development of resistant mutants in, for example, infected human patients. The mutant pathogens can spread to other persons, resulting in an outbreak of disease unresponsive to the particular drug. It is then necessary to use an alternate drug to treat the disease. The alternate drug will similarly be useful only until mutant pathogens resistant to the alternate drug begin to proliferate and dominate the population.

In many cases, drug-resistant pathogens are resistant to only a single drug or class of drugs. In recent years, however, an alarmingly rapid increase has been observed in the number of pathogens that have become multi-drug resistant, meaning that they are resistant to two or more, and in some cases many, classes of drugs. It may be only a matter of time before some pathogens become resistant to all available drugs. Since it can take many years to develop a new drug, there is an urgent need to obtain reliable, quantitative methods for avoiding spread and further development of drug-resistant pathogens.

The problem of drug resistance is especially acute among immunocompromised patients. In these patients, blocking the growth of pathogens by using doses based on the MIC is not adequate to clear the infection; resistant mutants grow and can be transmitted from the infected person to others. As AIDS has spread through regions of the world where tuberculosis is widespread, for example, drug-resistant tuberculosis strains have emerged and rapidly spread when the drug-resistant bacteria have subsequently infected healthy (i.e., immunocompetent) persons. The diseases caused thereby have proven resistant to traditional treatments.

Drug dosing schedules are often based on a parameter called the area under the curve (AUC), where the curve represents a plot of drug concentration in human serum versus the time after delivery of the antibiotic or other drug into the human. One currently favored approach to dosing within the pharmaceutical industry involves the analysis of an empirical parameter called the AUIC, defined as the ratio of the AUC to minimum inhibitory concentration (MIC). No sound theoretical basis has yet been identified as to why a drug maintained at a particular multiple of the MIC should clear an infection. Moreover, the AUIC concept has not been demonstrated to have any relationship to drug resistance.

SUMMARY OF THE INVENTION

Figure 1:
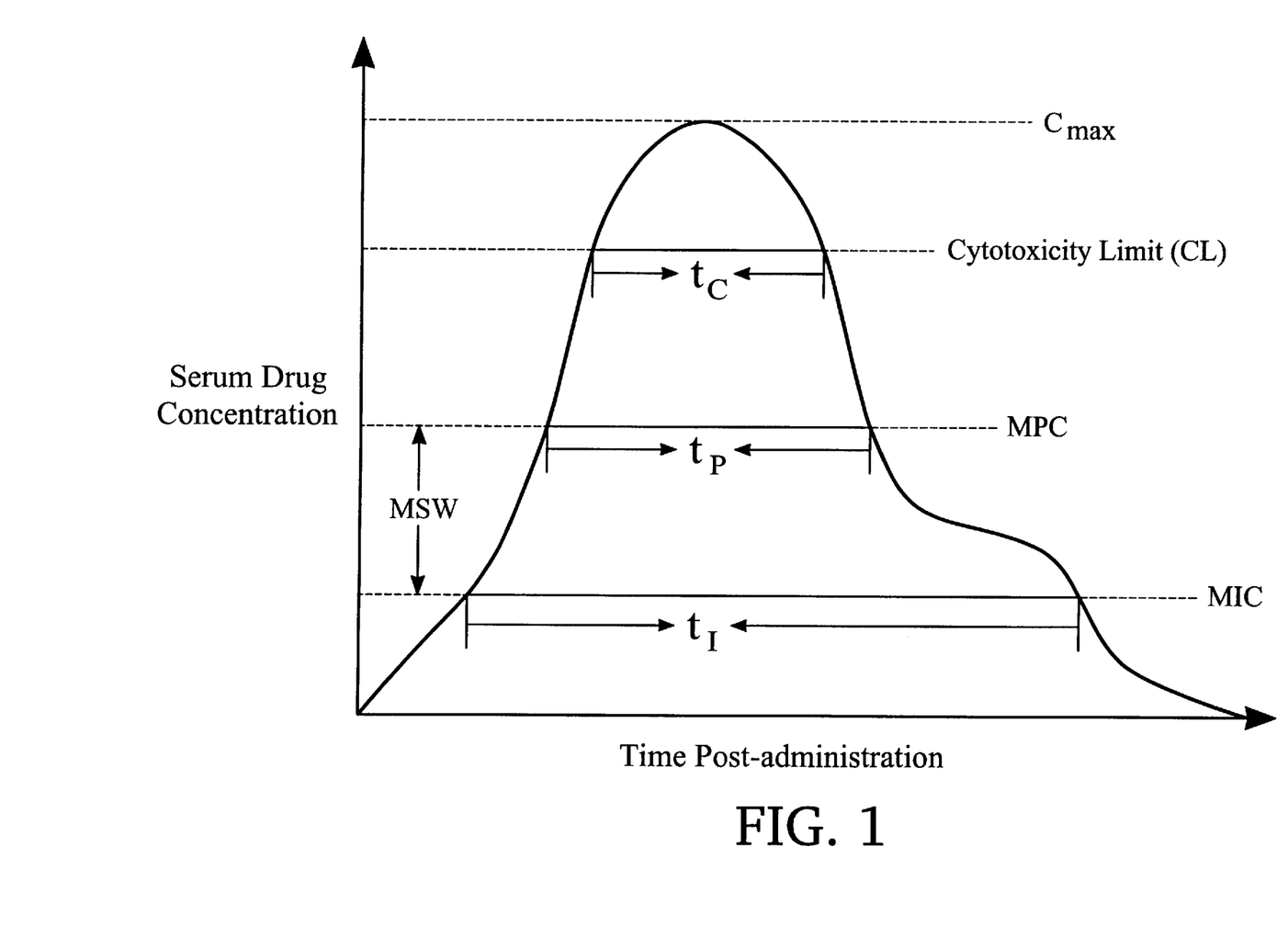
FIG. 1 is a hypothetical plot of serum drug concentration vs. time (i.e., post drug delivery to a patient) for various drug concentrations and times, illustrating MSW (i.e., the area in between the MIC and MPC)

The invention is based on the discovery that, for many drugs (e.g., antiviral or antimicrobial drugs such as antifungal or antibiotic drugs, including bacteriocidal or bacteriostatic drugs) and many pathogen strains (e.g., viral, fungal, or bacterial pathogens), a concentration of drug can be identified at which drug-resistant mutant pathogen strains are not selected. This concentration is herein referred to as the "mutant prevention concentration" (MPC). Maintaining serum concentrations of the drug above the MPC throughout a course of treatment should severely restrict selection of drug-resistant mutants. Additionally, it is discovered that drug-resistant mutant pathogens are selected exclusively within a drug concentration window, termed the "mutant selection window" (MSW; FIG. 1). A quantitative expression of this window, which we call the "window index" (WI), is defined as the ratio of the MPC to the MIC. The window index is characteristic of a given drug and a given pathogen.

In general, one embodiment of the invention features a method for determining the mutant prevention concentration (MPC) of a drug against a particular pathogen (e.g., a bacterial, fungal, or viral pathogen). The method includes the steps of obtaining a culture of said pathogen grown to high density (e.g., to stationary phase in the cases of bacteria and fungi); dividing at least some portion of the culture among a plurality (e.g., one, five, ten, one hundred, five hundred or more) of containers of a growth medium (e.g., agar plates) containing various concentrations of the drug; incubating the containers; counting the pathogen colonies (i.e., for bacteria or fungi), or plaques or foci (i.e., for viruses), if any, in the containers; plotting the number of counted colonies against drug concentration in each container; and, if necessary, extrapolating the plot to determine the minimum drug concentration corresponding to zero colonies. The minimum drug concentration corresponding to zero colonies is the MPC.

The invention also features a method for determining the mutant prevention concentration (MPC) of a drug against a particular pathogen (e.g., a bacterial, fungal, or viral pathogen). The method includes the steps of obtaining a culture of the pathogen, grown to high density (e.g., stationary phase), dividing at least some portion of the culture among a plurality (e.g., one, five, ten, one hundred, five hundred or more) of containers of a growth medium (e.g., agar plates, or a liquid culture broth) containing various concentrations of the drug; incubating the containers; and identifying the container having the lowest concentration of drug effective to prevent growth of the pathogen. This concentration is the MPC.

In any of the above methods: The culture can be concentrated or diluted, if necessary, prior to dividing among the containers. To refine measurement of the MPC, the method can be repeated with concentrations of drug more closely clustered around the MPC determined in the first iteration of the method.

The various concentrations of drug in the containers can differ from one another by a constant factor (e.g., ten-fold, five-fold, three-fold, or no more than about two-fold).

In the dividing step, between about $10^9$ and about $10^{12}$ colony-forming units (e.g., between about $10^{10}$ and about $10^{12}$ colony-forming units) of bacteria can be divided among all of the containers that include a single concentration of the drug. The number of containers required for each concentration in order to apply this number of bacteria will be understood to depend on the size of each container, and can vary from one to 100 or more.

In another embodiment, the invention features a method for determining the window index (WI) (i.e., corresponding to the mutant selection window for a drug wherein resistant mutants of a specific pathogen are selected in the presence of the drug). The method includes the steps of determining the minimum inhibitory concentration (MIC) of the drug for the pathogen; determining the mutant prevention concentration (MPC) of the drug for the pathogen; and dividing MPC by MIC to obtain the WI. WI can optionally be added to or multiplied by various constants.

The invention also features an improved method for selecting a suitable drug for treating an infection caused by a specific pathogen (e.g., a bacterial, fungal, or viral pathogen), where the method includes determining an MIC. The improvement comprises determining the window index (WI). The method can also include the step of selecting at least one drug (e.g., 1, 2, 3 or more, 10 or more, or 100 or more drugs) having a toxicity level greater than its MPC for the specific pathogen. Further, the method can include selecting at least one drug (e.g., 1, 2, 3 or more, 10 or more, or 100 or more drugs) having a window index (WI) less than thirty (e.g., less than about 30, less than about 20, less than about 10, less than about 5, or less than about 2).

The invention also features an improved method for screening a plurality of compounds against a specific pathogen (e.g., a bacterial, fungal, or viral pathogen), where the method includes determining an MIC. The improvement comprises determining the window index (WI) The method can also include the step of selecting from the plurality at least one drug (e.g., 1, 2, 3 or more, 10 or more, or 100 or more drugs) having a toxicity level greater than its MPC for the specific pathogen. Further, the method can include selecting from the plurality at least one drug (e.g., 1, 2, 3 or more, 10 or more, or 100 or more drugs) having a window index (WI) less than thirty (e.g., less than about 30, less than about 20, less than about 10, less than about 5, or less than about 2).

In still another embodiment, the invention features a method of treating a patient infected with a pathogen (e.g., a bacterial, fungal, or viral pathogen). The method includes the steps of determining the MPC of a drug against the pathogen; and administering the drug to the patient at a dosage and frequency sufficient for the drug concentration in the patient's serum to exceed the MPC. The dosage and frequency can be sufficient, for example, for $C_{max}$ to exceed the MPC, or sufficient to maintain serum concentration of the drug above the MPC in the patient for at least 5% (e.g., for at least 10%, at least 20%, at least 25%, at least 30%, at least 40%, at least 50%, at least 60%, at least 70%, at least 80%, at least 90%, at least 95%, at least 99%, or about 100%) of the duration of the treatment.

The duration of treatment is determined by conventional methods and is generally unchanged by this invention. One object of the invention is to prevent mutants from arising and/or proliferating during a course of treatment; this will not generally necessitate altering the duration of treatment.

The drug can include, for example, at least one of a bacteriostatic drug, a bacteriocidal drug, an aminoglycoside, an anphenicol, an ansamycin, a β-lactam, a lincosamide, a macrolide, a polypeptide antibiotic, a tetracycline, a cycloserine, a mupirocin, a tuberin, vancomycin, a 2,4-diaminopyrimidine, a nitrofuran, a quinolone, a fluoroquinolone, a sulfonamide, a sulfones, a fluoroquinolone, a macrolide, a tetracycline, an antifungal drug, an antiviral drug, or any derivative of any of these.

The patient can be, for example, a mammal (e.g., a human being) or a bird (e.g., a chicken). The drug can, for example, be administered in any form suitable for administration of drugs or medicaments (e.g., pills, tablets, chicken feed).

The invention also features a dosing regimen for a drug. The dosing regimen includes an administration level and frequency that maintains serum concentration in a treated subject below the toxicity level (e.g., cytotoxicity level CL) but above the MPC for at least 5% (e.g., for least 10%, at least 20%, at least 25%, at least 30%, at least 40%, at least 50%, at least 60%, at least 70%, at least 80%, at least 90%, at least 95%, at least 99%, or about 100%) of the time of a course of treatment.

As used herein, the term "drug" is to be understood to include, for example, both antimicrobial drugs and antiviral drugs. "Antimicrobial drugs" include, for example, all antibiotics and other antibacterial agents (e.g., bacteriostatic and bacteriocidal drugs), as well as antifungal drugs.

The term "pathogen" herein refers to, for example, any bacterium, fungus, or virus that can infect a patient. A "patient" can be, for example, a mammal (e.g., a primate such as a human; or a dog, a cat, a horse, a rabbit, a cow, a pig, or other mammal raised for human consumption or companionship), a fish (e.g., a salmon, a trout, a tuna, shellfish, a mollusk, or other fish raised for human consumption or companionship), or a reptile, amphibian, or bird (e.g., a snake, a frog, a chicken, a turkey, or other reptile, amphibian, or bird raised for human consumption or companionship).

Figure 2:
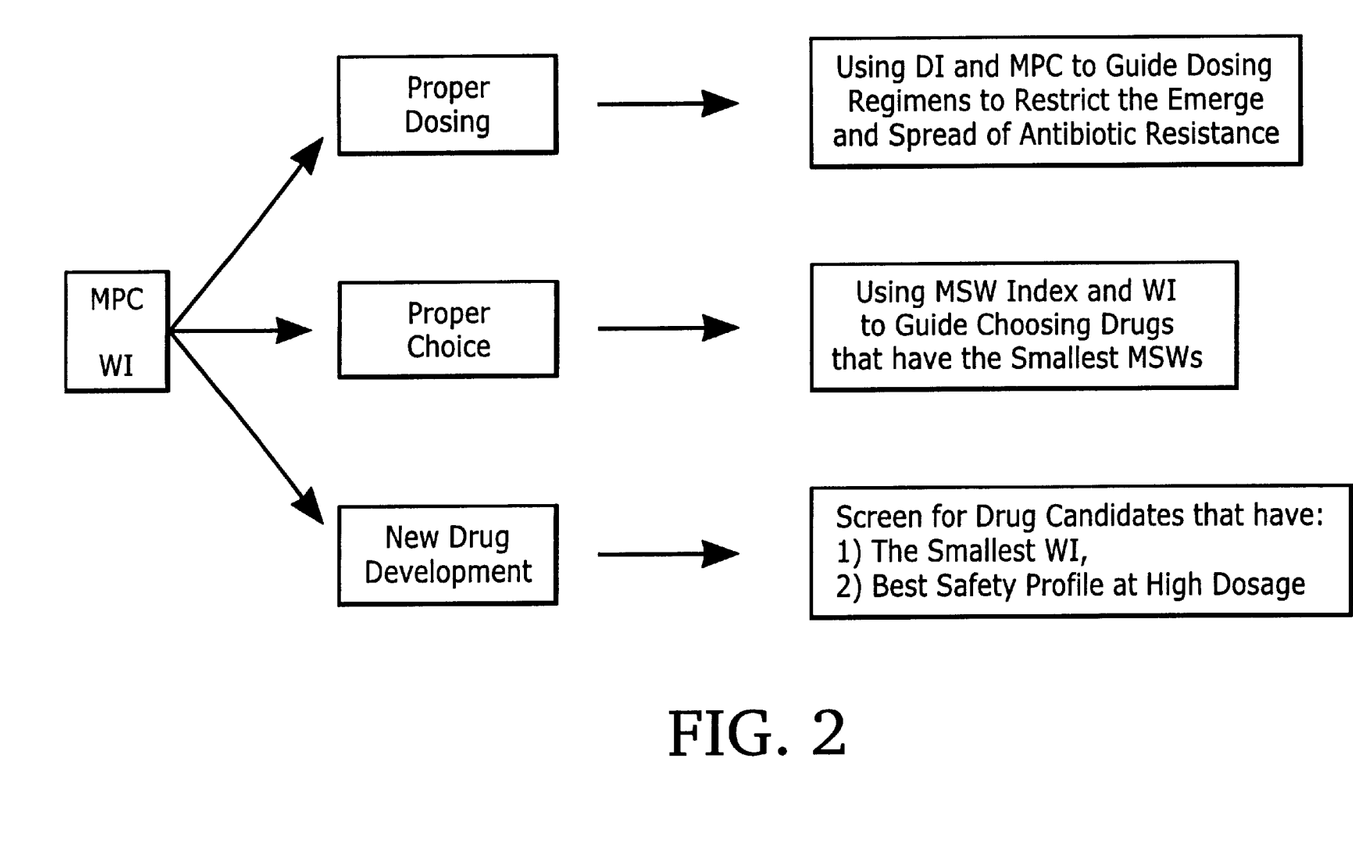
FIG. 2 is a chart illustrating the use of MPC and WI to restrict selection of mutant pathogens.

The invention provides several advantages. For example, the methods can define for pharmaceutical companies and physicians a drug concentration (i.e., MPC), which, if maintained in patient serum during treatment, will severely restrict, if not eliminate, the selection of resistant mutants (FIG. 2). Moreover, the MSW, which varies among pathogen species and antibiotics, can help guide suppliers, clinicians and/or researchers to the drug least likely to select resistant mutants through calculation of the window index (FIG. 2). The methods can additionally guide the development of new drugs, as the methods enable rapid identification of drugs that have relatively small window indices, affording a reduction in the likelihood that drug-resistant pathogen strains will arise and proliferate. Since MPC, MIC, and WI can be measured without knowledge of the mechanism of drug action and without having in hand resistant mutants to test, the WI and MPC concepts can be used at very early stages of drug development to find drugs that are least likely to allow resistance. WI and MPC can thus be used for the identification of superior compounds for drug development. MPC and WI data can also provide quantitative guidelines for clinicians, researchers, and pharmaceutical companies. Clinicians and researchers can use the data for selection and dosing of drugs. For example, $t_p$ (FIG. 1) is useful for dosing since it indicates how often a drug must be taken to keep serum concentrations above MPC. Researchers and pharmaceutical companies can use the data to guide development of drugs and dosing proposals and regimens.

Unless otherwise defined, all technical and scientific terms used herein have the same meaning as commonly understood by one of ordinary skill in the art to which this invention belongs. Although suitable methods and materials are described below, other methods and materials, similar or equivalent to those described herein, can also be used in the practice or testing of the present invention. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION
Mutant Prevention Concentration (MPC)

Figure 3:
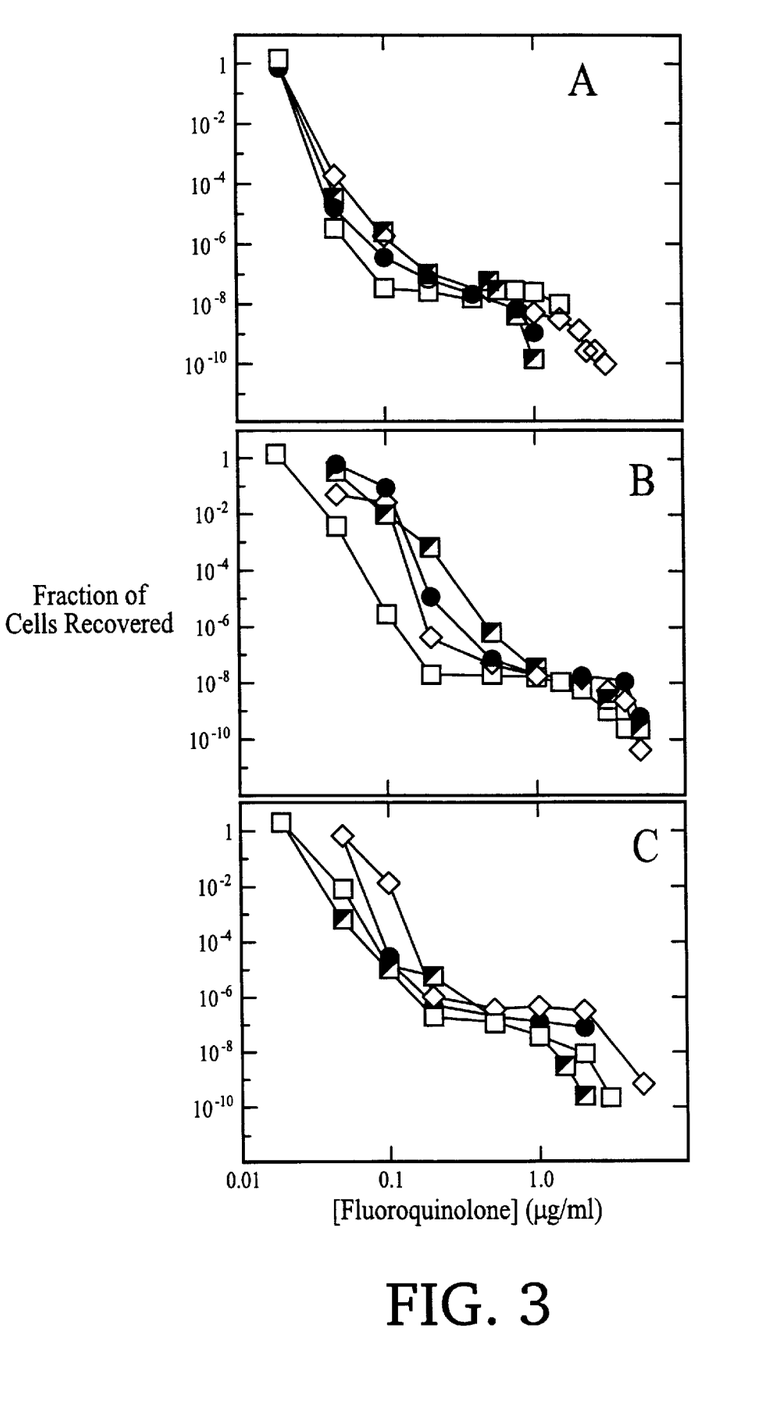
FIG. 3 is a set of plots of mutant selection curves for twelve fluoroquinolone compounds; the compounds represented in panels A, B, and C included C-8-methoxy, C-8-hydrogen, and C-8-fluorine moieties, respectively.
Figure 4:
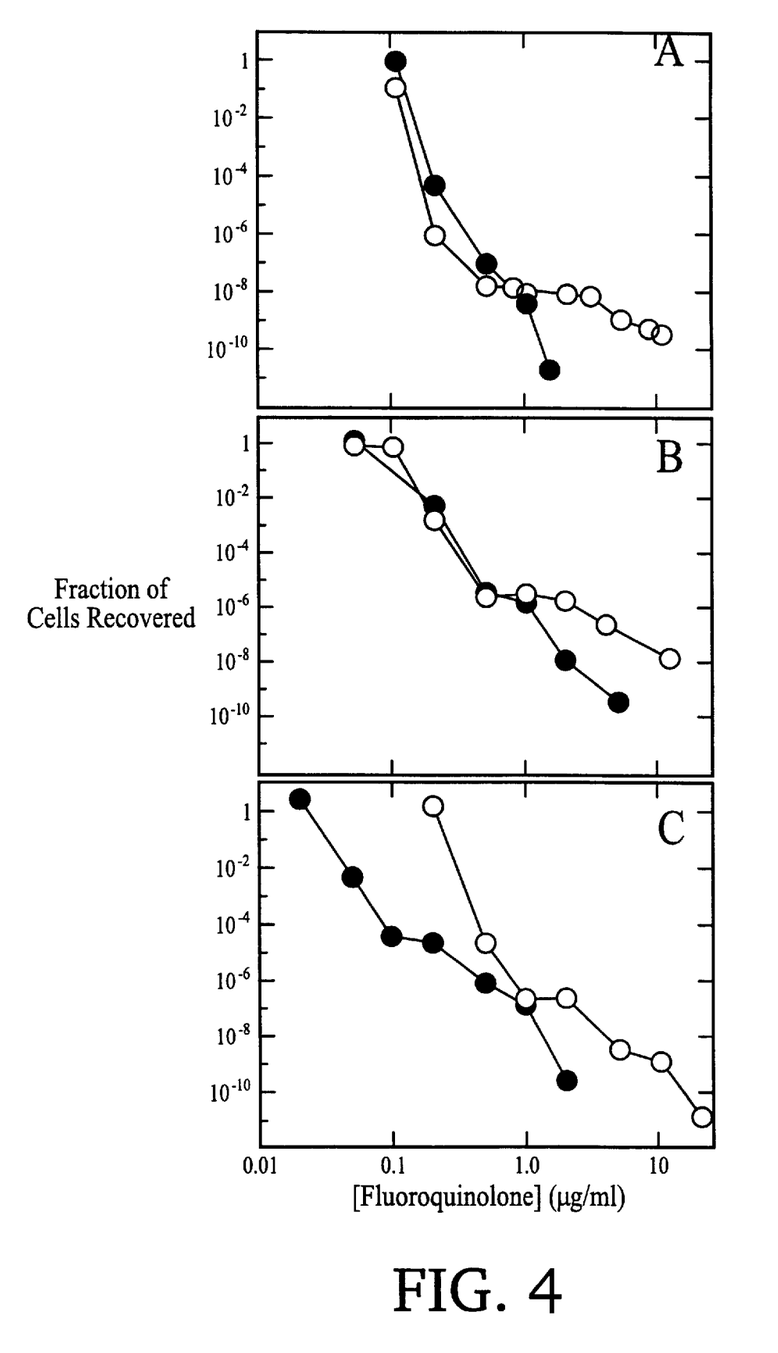
FIG. 4 is a set of plots of mutant selection curves for six fluoroquinolone compounds; the compounds represented in panels A, B, and C included C-8-methoxy, C-8-hydrogen, and C-8-fluorine moieties, respectively, but differed from the compounds represented in FIG. 3 at other positions.

A variety of drugs, specifically fluoroquinolones, were assayed at various concentrations for their ability to prevent selection of resistant mutants, using *Mycobacterium smegmatis* as a test organism. Large numbers of cells were applied to drug-containing agar plates, and the percentage that grew into colonies was determined. Results are presented in FIGS. 3 and 4. FIGS. 3 and 4 show that a sharp drop in recovery of colonies occurred above the MIC as wild-type growth was blocked, and then a plateau was observed. At the plateau concentrations, only mutants present in the sample grew out into colonies. Eventually, however, a drug concentration was reached at which a second sharp drop occurred. It is hypothesized that this second drop occurred as a result of the drug concentration exceeding the MIC of the most resistant first-step mutant. Although not wishing to be bound by any theory, our logic is as follows: Above the MIC of the most resistant mutant, only double mutants grow into colonies. To create double mutants, wild-type cells must acquire two concurrent mutations, an event so rare as to be virtually undetectible. For example, the frequency of a single mutation is generally about $10^{-8}$ for antibacterial agents such as fluoroquinolones. The frequency of a double mutation should thus be about $(10^{-8})^2$, or $10^{-16}$. A population of about $10^{16}$ cells, or about 10,000 liters of stationary phase culture, enough to provide 10 million agar plates with $10^9$ cells per plate, would be required, on average, to obtain a double mutant. The volume occupied by $10^{16}$ cells at $10^9$ cells per milliliter exceeds the volume of over 100 human bodies. Thus, dosing at a concentration above the MIC of the most resistant mutant will as a practical matter effectively block selection of drug-resistant bacteria. The concentration at and above which no mutant are recovered when a large number of cells is applied to the plate we call the "mutant prevention concentration" (MPC).

FIGS. 3 and 4 show that a mutant selection curve was observed for various drugs tested and that the compounds are readily distinguished by the shapes of the curves.

Figure 5:
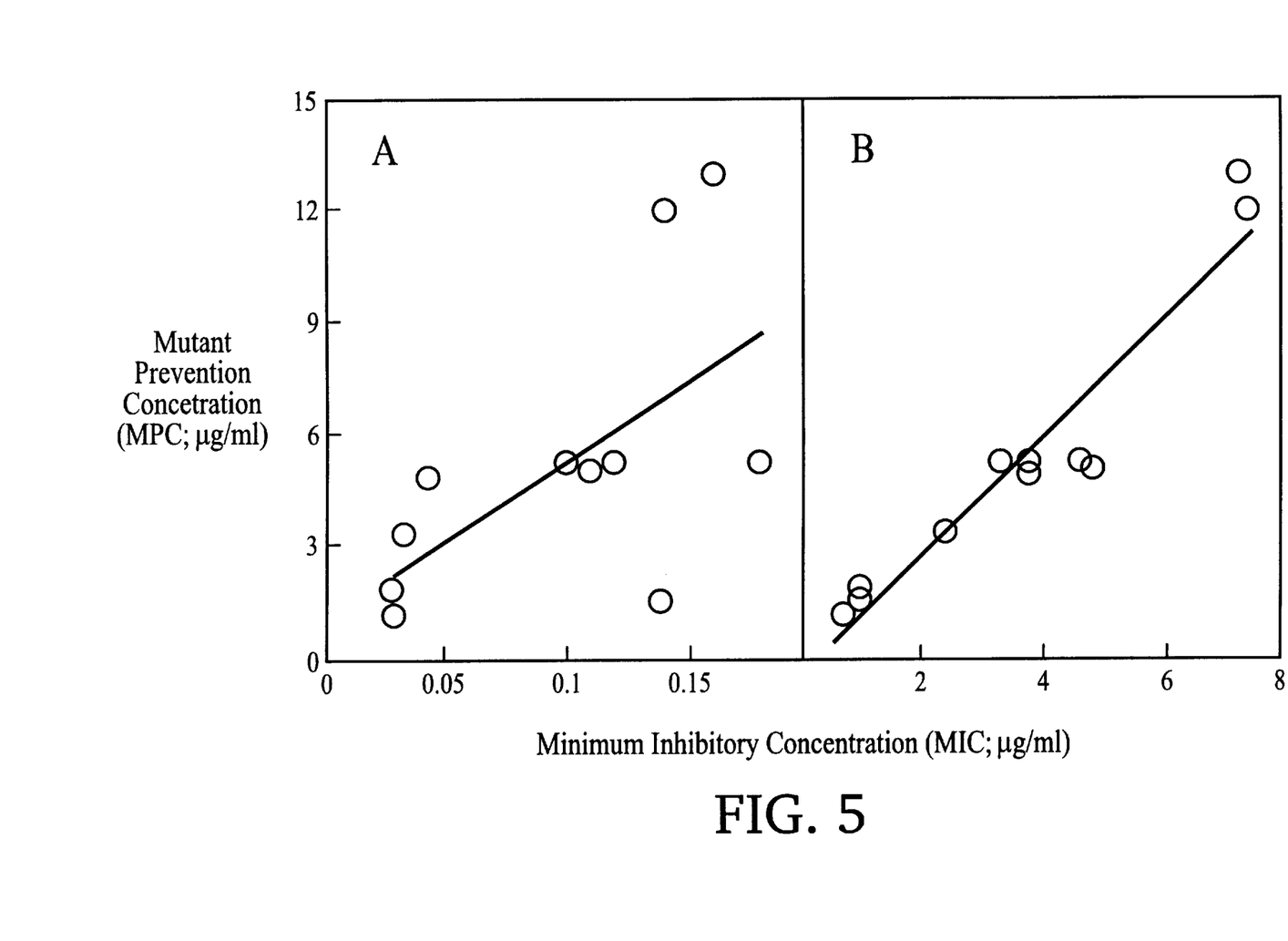
FIG. 5 is a set of plots illustrating the relationship between MPC and MIC of wild-type (FIG. 5A) and first-step mutant cells (FIG. 5B)

For some drugs, but certainly not all, the MIC of wild-type cells correlates weakly with MPC (FIG. 5A). In contrast, a much stronger correlation is observed between MPC and the MIC of the most resistant first-step mutant (FIG. 5B). For many bacteria, the most resistant first-step mutant is unavailable for comparing the ability of compounds to restrict selection of mutants. Thus, direct measurement of MPC may be the best way to evaluate the effects of structure refinements on selection of resistant mutants.
Mutant Selection Window and the Window Index A typical serum concentration versus time curve is shown in FIG. 1. For a pharmacological response to occur in an organ or tissue away from the immediate site of absorption, a drug has to be carried there by the blood. The intensity and duration of the tissue response is generally a function of the concentration and stability of the drug in blood or serum. As shown in FIG. 1, serum concentration rises and falls with a characteristic pattern. The rise in serum concentration occurs during an "absorption" phase, while the decrease occurs in an "elimination" phase. The decline in concentration with time can be measured to give the pharmacokinetic half-life (the time taken for the concentration to decline to half of its peak value). The maximal concentration of the drug in the serum is termed "$C_{max}$"; the minimum concentration of the drug is "$C_{min}$".

Efforts are underway to define dosing parameters that will guide treatment with antibiotics. One approach is to divide the area under the curve (AUC) by the MIC. Empirically, it has been found that when this number is about 100 for certain members of the fluoroquinolone family of antibacterial agents, bacterial infections tend to be cleared by the antibiotic treatment. Generally, no consideration is given to preventing resistance from arising. Indeed, as pointed out below, current dosing strategies can lead directly to the selection of resistance, as antibiotic drugs are often administered at doses within the mutant selection window (MSW; FIG. 1) to keep serum drug concentrations far from the cytotoxicity limit (CL). Consideration of MPC allows selection of resistance to be avoided.

In FIG. 1, MSW is illustrated graphically as the area between the MIC and the MPC. A quantitative expression of MSW, which we call the "MSW index", can be defined as the ratio of the MPC to the MIC, multiplied by a time factor $t_w$. Factor $t_w$ can be estimated by taking the average of $t_p$ and $t_i$, where $t_p$ and $t_i$ are the time durations in which serum drug concentration exceeds MPC and MIC, respectively. In FIG. 1, $t_c$ is the time duration in which serum drug concentration exceeds the cytotoxicity limit. Cytotoxicity is determined by methods well known to those of ordinary skill in the art. The MSW index is characteristic of a given drug and a given pathogen.

The magnitude of MSW depends on $t_w$, MIC, and MPC, and can be reduced (or entirely closed) by decreasing either $t_w$ or the MSW/MIC ratio. Because of practical dosing considerations, there is a lower limit for $t_w$. Moreover, $t_w$ cannot be determined prior to determination of MPC and MIC. A simplified term, window index (WI), has been defined above as the ratio of MPC to MIC. Since WI differs from MSW index by a constant factor and does not require determination of $t_w$, WI is found to be conveniently used in place of the MSW index in the methods of the invention. It is to be understood, however, that MSW index, or any other index related to WI by multiplying by or adding a constant, can equivalently be used in the claimed methods pertaining to WI.

Different drugs may have such widely different MIC and MPC values against a given pathogen that the use of absolute differences between MIC and MPC may have little practical significance. This absolute difference can be divided by MIC to obtain an index equal to WI minus one. It is comtemplated that the latter index can be WI in the practice of the claimed methods.

Only within the MSW can mutants be selected: at concentrations below the MIC, no mutants will be selected, because there is no selection pressure; above the MPC, no mutants will be selected because a rare double mutation would be required.

To prevent the selection of resistant mutants, serum concentration must be maintained above the MPC, i.e., outside the MSW for sufficient duration to outpace mutant growth. Moreover, $C_{max}$ must be below the cytotoxicity limit. A "dosing index" (DI) is defined as the difference between CL and MPC, divided by MPC, or (CL-MPC)/MPC. Larger DI values facilitate development of safe dosing regimens. Drugs having a negative DI, meaning that CL<MPC, would be of little use in avoiding selection of mutants.

The MSW can also be important when considering the appropriate drug for inhibiting growth of a given pathogen. When we determined the MPC for several pathogens using a variety of drugs, we found that the window index varied considerably (Table 1). For example, when tested against *Staphylococcus aureus*, rifampicin had a window index greater than 120,000, and chloramphenicol had a window index of about 21.

Window index measurements can be useful for comparing either widely different drug families (Table 1) or closely related members of the same drug family (Table 2). Such measurements constitute a new way to evaluate drugs. As described above, the magnitude of the window index varies from drug to drug, and this fact can be used advantageously for the development of compounds that will restrict selection of pathogen resistance: the smaller the window index, the lower the chance that resistance will arise. Since serum drug concentration can fluctuate among different patients, and patients may occasionally miss doses, drugs having a relatively small window index are likely to be most useful in preventing the selection of drug-resistant mutants. Thus, the window index is likely to have clinical significance for choosing the drug least likely to select for resistance.

TABLE 1

|  | MIC[a] | MPC[b] | WI (MPC/MIC) |
|---|---|---|---|
| *Escherichia coli* | | | |
| Norfloxacin | 0.045 | 1.5 | 33 |
| Tobramycin | 1.2 | 25 | 21 |
| Chloramphenicol | 1.9 | 12 | 6.3 |
| Rifampicin | 5 | >4,000 | >800 |
| Penicillin[d] | 3 | 300 | 100 |
| *Staphylococcus aureus* | | | |
| Norfloxacin | 0.85 | 22 | 26 |
| Tobramycin | 0.27 | 20 | 74 |
| Chloramphenicol | 1.9 | 40 | 21 |
| Rifampicin | 0.004 | 480 | 120,000 |
| Penicillin[c] | 0.024 | 1 | 42 |
| Vancomycin | 0.65 | 40 | 61 |

[a]$MIC_{99}$ μG/ml
[b]$MPC_{10}^{10}$ μg/ml
[c]specific activity: 1,6000 units/mg

TABLE 2

| Fluoroquinolone | MIC* | MPC** | WI (MPC/MIC) |
|---|---|---|---|
| Norfloxacin | 0.31 | 7 | 23 |
| Ciprofloxacin | 0.12 | 0.9 | 7.5 |
| HE1 | 0.21 | 1 | 4.8 |
| OE1 | 0.11 | 0.4 | 3.6 |

*$MIC_{99}$ (μg/ml)
**$MPC_{10}^{10}$ (μg/ml)

Given a situation in which a pathogen is found to be susceptible to, for example, three different drugs, it is generally advantageous to select the drug having the smallest window index, provided that the MPC is below the toxicity level for the drug. This strategy can greatly reduce the probability that a concentration within the MSW will exist for a duration sufficient for drug-resistant mutants to grow. When possible, it can also be advantageous to select a first dose that will cause the serum drug concentration to quickly pass through the MSW, in order to avoid selection of resistance at the early stages of treatment.

EXAMPLES

The following examples provide specific methods for making and using the invention and do not limit the invention's scope.

Example 1

Use of MPC to Evaluate Quinolone Susceptibility Among Clinical Isolates of *M. tuberculosis*

Strains of *M. tuberculosis* collected from both the United States and Russia were screened. To maximize diversity, test isolates were chosen to have different IS6110 DNA types (DNA fingerprints). The isolates were compared by measuring MIC and MPC.

Figure 6:
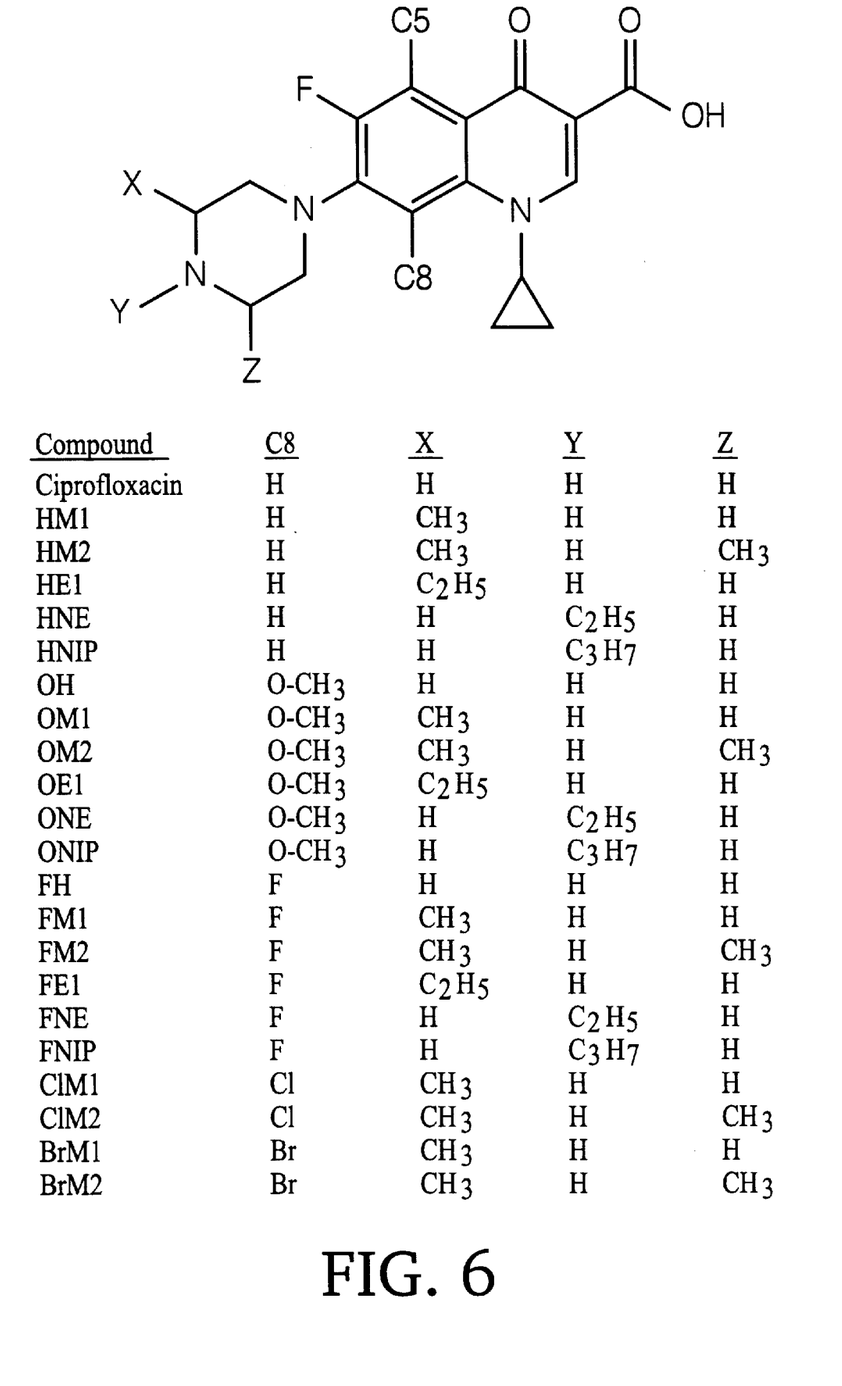
FIG. 6 is a depiction of the fluoroquinolones tested in the experiments described in Examples 1 and 2.
Figure 7:
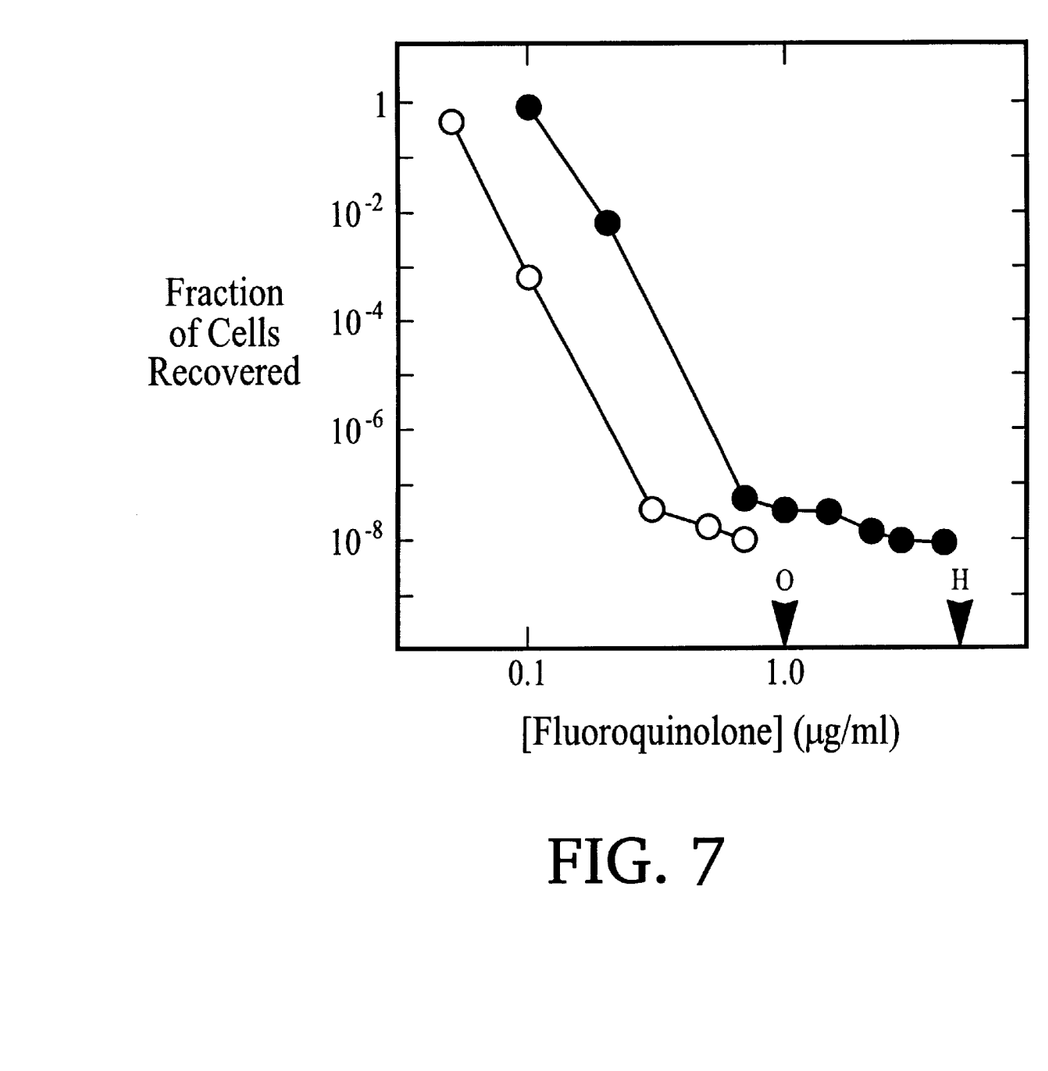
FIG. 7 is a plot of mutant selection curves for two fluoroquinolone compounds assayed against *Mycobacterium tuberculosis*, with arrow heads indicating concentrations at which no mutants were recovered.

The fluoroquinolones OE1 and HE1 in FIG. 6 were provided by Parke-Davis Pharmaceutical Co. *M. tuberculosis* was cultured in Middlebrook 7H9 liquid medium enriched with 10% albumin-dextrose complex and 0.05% TWEEN-80; Middlebrook 7H10 agar plates were used for single-colony isolation, MIC determination, and measurement of colony-forming units (CFU) according to the methods of Jacobs, W. R. et al., *Methods Enzymol.* 204:537–555, 1991. Resistant mutants were selected by incubation of cultures spread on 7H10 agar plates containing various concentrations of fluoroquinolone, as described in Dong, Y. et al., *Antimicrob. Agents Chemother.* 43:1756–1758, 1999.

For selection, the bacteria were grown to stationary phase in liquid medium, concentrated by centrifugation (3,000× g for 10 min), resuspended in fresh 7H9 medium, and applied to agar plates in 1 ml aliquots at an estimated concentration of about $2\times10^9$ CFU/ml.

Colonies were counted after incubation at 37° C. for 4 weeks. The concentration that prevented recovery of colonies was taken as MPC. MIC was determined by plating two-fold dilutions of cultures on agar plates containing various concentrations of fluoroquinolone. The concentration that reduced the number of colonies recovered by at least 99% relative to untreated controls was taken as the MIC.

Against all strains tested, a C8-methoxy group reduced the MIC by half (Table 3). MIC exhibited no relationship with genotypic grouping or IS6110 DNA polymorphism type. The average MIC for the Russian isolates was found to be 40% of that of United States isolates (Table 3).

To assess the effect of drug concentration on mutant selection, *M. tuberculosis* mutants arising on agar plates containing various concentrations of fluoroquinolone were counted. As shown in FIG. 7, increasing the fluoroquinolone concentration caused mutant recovery to decline sharply, level to a plateau, and then decline sharply a second time. Zero points, indicated by arrow heads, cannot be plotted on log plots; thus, the second sharp drop is not shown by a line in FIG. 7. Nevertheless, a second drop was clear. The C-8-methoxy compound generally allowed fewer mutants to be recovered at a given fluoroquinolone concentration. In each case a concentration was found at which no mutant was obtained on agar plates containing the C-8-methoxy compound, even though hundreds of colonies were recovered from plates containing the C-8-H derivatives (FIG. 7). Curves similar to those shown in FIG. 7 were obtained for all 13 strains. The concentration required to prevent mutant recovery, MPC, was found to be at least two times higher for the C-8-H compound in each case (Table 3). These results showed via MPC measurements that a C-8-methoxy fluoroquinolone was more likely to be effective against a wide variety of M. tuberculosis strains than a C-8-H compound.

TABLE 3

| Isolate Number | IS6110 type[a] | Genotype Group[b] | Source location[c] | antibiotic resistance[d] | MIC[e] OE1 | MIC[e] HE1 | MPC[f] OE1 | MPC[f] HE1 |
|---|---|---|---|---|---|---|---|---|
| TN1626 | W | 1 | NY | I,S,R, Em, Kn | 0.1 | 0.2 | 1 | >4.5 |

TABLE 3-continued

| Isolate Number | IS6110 type[a] | Genotype Group[b] | Source location[c] | antibiotic resistance[d] | MIC[e] OE1 | MIC[e] HE1 | MPC[f] OE1 | MPC[f] HE1 |
|---|---|---|---|---|---|---|---|---|
| TN3541 | DV | 1 | NY | I,R, Em | 0.2 | 0.4 | >2.25 | >7.0 |
| TN5702 | Unique | 1 | NJ | I | 0.4 | 0.8 | >4 | >10 |
| TN5704 | Unique | 1 | NJ | I | 0.2 | 0.4 | 2.25 | >4.5 |
| TN7804 | W148 | 1 | Russia | I,S,R, Et,Kn | 0.1 | 0.2 | 1 | >4.5 |
| TN1865 | H | 2 | NY | None | 0.3 | 0.6 | >3.0 | >7.5 |
| TN5410 | Unique | 2 | NJ | None | 0.2 | 0.4 | 2.25 | >5.5 |
| TN7791 | Unique | 2 | Russia | I | 0.1 | 0.2 | 1.5 | 4.5 |
| TN5355 | Unique | 3 | NJ | None | 0.2 | 0.4 | 2.25 | >5.5 |
| TN2156 | Co | nd | NY | None | 0.3 | 0.6 | 3.5 | >7.0 |
| TN7834 | Unique | 3 | Russia | None | 0.1 | 0.2 | 2.25 | >5.5 |
| TN7811 | Unique | 3 | Russia | S,Kn | 0.1 | 0.2 | 1 | >4.5 |
| TN7829 | Unique | 3 | Russia | None | 0.1 | 0.2 | 2.25 | >5.0 |

[a]IS6110 DNA pattern is as in (7).
[b]Genotype group is as described in (Srinand, S., 1997).
[c]From PHRI TB Center
[d]Isolates were resistant to indicated antibiotics: I, isoniazid; S, streptomycin; R, rifampicin; Em, ethambutol; Kn, kanamycin; Et, ethionamide.
[e]Minimum inhibitor concentration (μg/ml).

Example 2

Use of MPC to Compare Fluoroquinolone Potency

Against *M. bovis* BCG, the MPC of a C-8-methoxy fluoroquinolone was found to be eight times lower than that of a C-8-hydrogen derivative. Addition of a methoxy group to the C-8 position of N-1-cyclopropyl fluoroquinolones rendered the compounds particularly active against quinolone-resistant gyrA (gyrase) mutants of *M. bovis* BCG.

More extensive studies were then performed with *Mycobacterium smegmatis*. Relevant features of *M. smegmatis* $mc^2$ 155 and its gyrA mutants are listed in Table 4.
Cells were grown as liquid cultures in Middlebrook 7H9 medium containing 10% albumin dextrose complex (ADC) and 0.05% Tween 80. Colonies were grown on Middlebrook 7H10 agar plates. Agar plates containing fluoroquinolone were prepared by adding concentrated solutions to molten agar. Incubation temperature for growth was 37° C.

TABLE 4

| Strain | Relevant genotype[a] | Source or reference |
|---|---|---|
| | *M. smegmatis* | |
| KD1163 | $mc_2$ 155 (wild type) | S. Cole Ref |
| DK1987 | KD1163 gyrA (A91V) | This work |
| DK1991 | KD1163 gyrA (D95Y) | This work |
| KD1995 | KD1163 gyrA (D95H) | This work |
| KD1998 | KD1163 gyrA (D95N) | This work |
| DK1999 | KD1163 gyrA (D95A) | This work |
| KD2003 | KD1163 gyrA (D95G) | This work |
| KD2008 | KD1163 gyrA (G89C) | This work |
| KD2012 | KD1163 gyrA (G89A) | This work |
| | *M. tuberculosis* | |
| TN1625 | gyrA* | PHIR TB Center (5,6) |

[a]Amino acid abbreviations: A, alanine; D, aspartic acid; C, cysteine; H, histidine; G, glycine; N, asparagine; V, valine; and Y, tyrosine. The first letter represents the wild-type amino acid at the position indicated by the number. The second letter indicates the identity of the mutant amino acid at that position.

To assay the selection of fluoroquinolone-resistant mutants, *M. smegmatis* was grown to stationary phase (Klett=350), harvested by centrifugation, and resuspended in the same volume of fresh growth medium. Incubation was continued until the turbidity of the culture reached Klett=400 to 450, and the culture was again concentrated by centrifugation (6,000× g for 15 min). Cells were resuspended to about $10^9$ CFU/ml in growth medium and then applied at various volumes and concentrations to fluoroquinolone-containing 7H10 agar. The plates were allowed to dry in a biosafety cabinet for about 30 min at room temperature, sealed with electrical tape to minimize evaporation, and inverted for incubation at 37° C. for 3–7 days. After colonies were counted, they were confirmed to be resistant mutants by regrowth on fluoroquinolone-containing agar.

MIC was determined graphically from log-log plots of fluoroquinolone concentration versus colony number. For this measurement, 7H10 agar plates containing various concentrations of fluoroquinolone were prepared in a biosafety cabinet. Stationary phase cells (Klett=450) were diluted in EPPENDORF™ tubes by 10-fold increments using 7H9 liquid medium as diluent. 10 $\mu$l portions were spotted on plates. Colonies on each plate were counted after incubation for 5 to 7 days at 37° C. In these experiments, MIC was defined as the fluoroquinolone concentration required to inhibit colony formation by 99%. MIC was determined by interpolation from double log plots of fluoroquinolone concentration versus fraction of colony-forming units recovered.

Fluoroquinolones (10 mg) were dissolved in 0.1 ml 1 N sodium hydroxide (1/10 of final volume), and then sterile water was added to give a final concentration of 10 mg/ml. This stock solution was divided into 50 ul aliquots and stored at −80° C. Dilution series were prepared with autoclaved water. Solutions were occasionally stored at −20° C. for several weeks.

To compare the compounds for selection of resistant mutants, about $10^{10}$ cells were plated on agar containing various fluoroquinolone concentrations. The number of mutant colonies that arose was counted. As shown in FIGS. 3 and 4, the number of mutants dropped sharply at concentrations slightly above the MIC. At higher concentrations a plateau was seen for many compounds, followed by a second sharp drop at very high concentrations.

Results obtained with four compounds that had similar values of MIC are shown in FIG. 3A. The compounds differed in the concentration at which the high-concentration drop in recovery occurred: the compound with the monomethyl substituent on the C-7 ring was the most effective, followed by the ethyl, dimethyl, and N-ethyl compounds (FIG. 3A).

Figure 8:
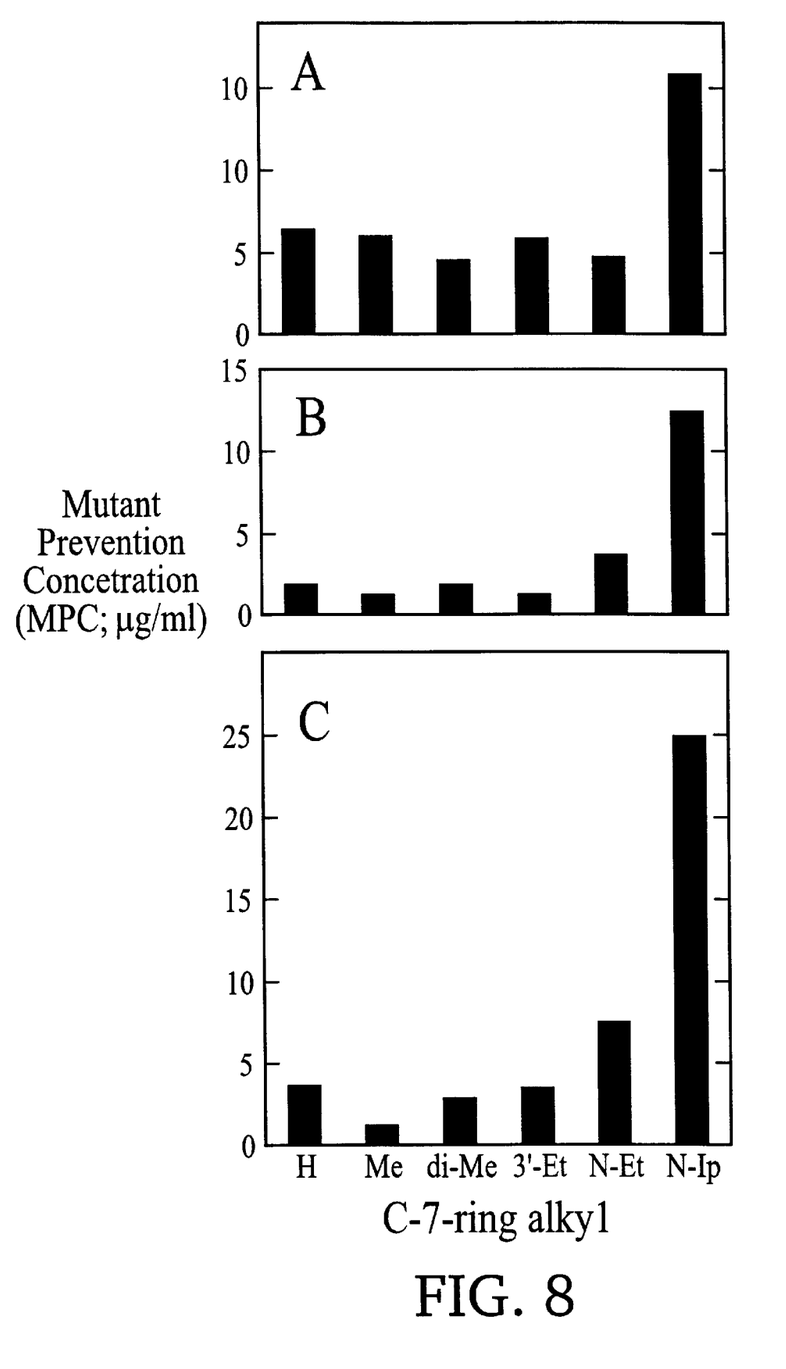
FIG. 8 is a set of bar charts illustrating the effects of various fluoroquinolone compounds on MPC when assayed against *Mycobacterium smegmatis*; the compounds represented in panels A, B, and C included C-8-hydrogen, C-8-methoxy, and C-8-fluorine moieties, respectively.

MPC for the C-8-H series showed little difference among the compounds having small alkyl groups; in contrast, the N-isopropyl compound exhibited a much higher value (FIG. 8A). For the C-8-OMe compounds, various C-7 ring substituents also had similar effects, except that N-ethyl and N-isopropyl groups required higher concentrations to block mutant recovery (FIG. 8B). The C-8-F series exhibited a distinct minimum with the monomethyl derivative; the N-ethyl and N-isopropyl derivatives were less active by this assay (FIG. 8C).

Figure 9:
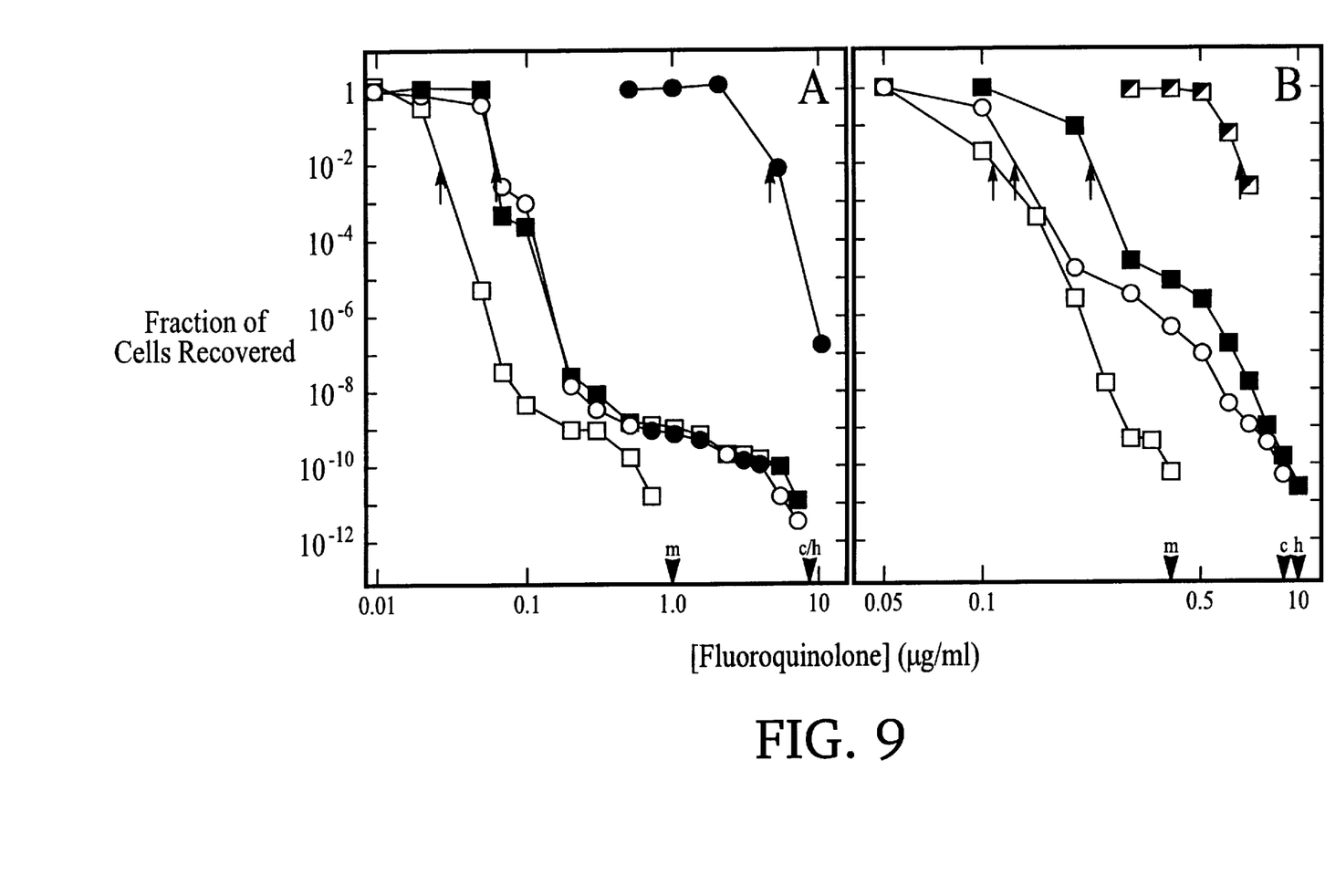
FIG. 9 is a set of plots of recovery of fluoroquinolone resistant mutants of *Mycobacterium bovis* (FIG. 9A) and *Staphylococcus aureus* (FIG. 9B).

As indicated above, work with *M. bovis* BCG showed that a C-8-OMe group increased the activity of fluoroquinolones against a first-step gyrA mutant of *M. bovis* BCG (FIG. 9A). A similar effect was seen with Staphylococcus aureus (FIG. 9B).

This survey of 18 closely related fluoroquinolones identified the C-8-methoxy C-7-ring monomethyl compound as the most potent against the fast-growing species, *M. smegmatis*. When *M. tuberculosis* was used to compare that compound against a derivative that had previously shown good activity, the new compound was clearly more potent by the MPC test. Thus, the MPC test using *M. smegmatis* can be used to identify superior anti-tuberculosis fluoroquinolones. Moreover, the MPC with *M. tuberculosis* was below the maximum serum level commonly achieved by fluoroquinolones. Thus, it is feasible to maintain that level above the MPC and thereby prevent resistance.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a patient infected with a pathogen, the method comprising:

administering to the patient a drug at a dosage and frequency sufficient for the serum concentration of said drug to exceed the mutant prevention concentration (MPC) in said patient, thereby treating said patient, wherein said MPC is a concentration determined by a method comprising applying at lease 1010 colony-, plaque- or foci-forming units of a pathogen to a plurality of containers, wherein said containers contain differing concentrations of said drug, incubating said containers, counting the pathogen colonies, plaques, or foci in said cultures, plotting the number of counted colonies, plaques, or foci against the drug concentration; and extrapolating or interpolating the plot to determine the minimum drug concentration corresponding to zero colonies, plaques, or foci, said minimum drug concentration being the MPC.

2. The method of claim 1, wherein said dosage and frequency are sufficient to maintain serum concentration of said drug above the MPC in said patient for at least 10% of the duration of said treating.

3. The method of claim 1, wherein said dosage and frequency are sufficient to maintain serum concentration of said drug above the MPC in said patient for at least 25% of the duration of said treating.

4. The method of claim 1, wherein said dosage and frequency are sufficient to maintain serum concentration of said drug above the MPC in said patient for at least 50% of the duration of said treating.

5. The method of claim 1, wherein said dosage and frequency are sufficient to maintain serum concentration of said drug above the MPC in said patient for at least 75% of the duration of said treating.

6. The method of claim 1, wherein said dosage and frequency are sufficient to maintain serum concentration of said drug above the MPC in said patient for at least 90% of the duration of said treating.

7. The method of claim 1, wherein said dosage and frequency are sufficient to maintain serum concentration of said drug above the MPC in said patient for at least 95% of the duration of said treating.

8. The method of claim 1, wherein said dosage and frequency are sufficient to maintain serum concentration of said drug above the MPC in said patient for at least 99% of the duration of said treating.

9. The method of claim 1, wherein said drug comprises at least one bacteriostatic drug.

10. The method of claim 1, wherein said drug comprises at least one bacteriocidal drug.

11. The method of claim 1, wherein said drug comprises at least one antibiotic selected from the group consisting of aminoglycosides, anphenicols, ansamycins, β-lactams, lincosamides, macrolides, polypeptide antibiotics, tetracyclines, cycloserine, mupirocin, tuberin, and vancomycin.

12. The method of claim 1, wherein said drug comprises at least one antibiotic selected from the group consisting of 2,4-diaminopyrimidines, nitrofurans, quinolones, fluoroquinolones, sulfonamides, and sulfones.

13. The method of claim 1, wherein said drug comprises at least one fluoroquinolone antibiotic.

14. The method of claim 1, wherein said drug comprises at least one macrolide antibiotic.

15. The method of claim 1, wherein said drug comprises at least one tetracycline antibiotic.

16. The method of claim 1, wherein said drug comprises at least one antifungal drug.

17. The method of claim 1, wherein said drug comprises at least one antiviral drug.

18. The method of claim 1, wherein said patient is a human being.

19. The method of claim 1, wherein said patient is a chicken, and said drug is administered via chicken feed.

* * * * *